United States Patent

Giurtino

[11] Patent Number: 5,938,685
[45] Date of Patent: Aug. 17, 1999

[54] LOCKING HANDLE FOR SURGICAL INSTRUMENTS

[75] Inventor: Joel F. Giurtino, Miami, Fla.

[73] Assignee: Boston Scientific Corporation, Natick, Mass.

[21] Appl. No.: 08/924,745

[22] Filed: Sep. 5, 1997

[51] Int. Cl.$^6$ .................................................. A61B 17/28
[52] U.S. Cl. ............................................. 606/208; 81/339
[58] Field of Search .................................. 606/208, 207, 606/206, 205; 81/339, 340, 314, 315, 329

[56] References Cited

U.S. PATENT DOCUMENTS

| | | | |
|---|---|---|---|
| 1,944,116 | 1/1934 | Stratman | 81/339 |
| 2,539,865 | 1/1951 | Sarvie | 81/339 |
| 4,787,279 | 11/1988 | Undin | 81/313 |
| 4,896,661 | 1/1990 | Bogert et al. | 606/86 |
| 5,174,300 | 12/1992 | Bales et al. | 128/751 |
| 5,176,702 | 1/1993 | Bales et al. | 606/208 |
| 5,209,747 | 5/1993 | Knoepfler | 606/16 |
| 5,217,460 | 6/1993 | Knoepfler | 606/52 |
| 5,235,966 | 8/1993 | Jamner | 128/20 |
| 5,269,797 | 12/1993 | Bonati et al. | 606/170 |
| 5,281,220 | 1/1994 | Blake, III | 606/46 |
| 5,308,357 | 5/1994 | Lichtman | 606/205 |
| 5,318,589 | 6/1994 | Lichtman | 606/205 |
| 5,342,381 | 8/1994 | Tidemand | 606/174 |
| 5,342,391 | 8/1994 | Foshee et al. | 606/205 |
| 5,352,237 | 10/1994 | Rodak et al. | 606/206 |
| 5,354,312 | 10/1994 | Brinkerhoff et al. | 606/207 |
| 5,383,888 | 1/1995 | Zvenyatsky et al. | 606/206 |
| 5,408,904 | 4/1995 | Neff | 81/360 |
| 5,409,478 | 4/1995 | Gerry et al. | 606/1 |
| 5,470,328 | 11/1995 | Furnish et al. | 606/1 |
| 5,476,479 | 12/1995 | Green et al. | 606/205 |
| 5,480,409 | 1/1996 | Riza | 606/205 |
| 5,483,952 | 1/1996 | Aranyi | 600/131 |
| 5,496,347 | 3/1996 | Hashiguchi et al. | 606/205 |
| 5,562,655 | 10/1996 | Mittelstadt et al. | 606/1 |
| 5,562,682 | 10/1996 | Oberlin et al. | 606/139 |
| 5,573,530 | 11/1996 | Fleury et al. | 606/1 |
| 5,578,032 | 11/1996 | Lalonde | 606/54 |
| 5,603,723 | 2/1997 | Aranyi et al. | 606/205 |
| 5,735,874 | 4/1998 | Measamer et al. | 606/208 |

Primary Examiner—Michael Buiz
Assistant Examiner—Julian W. Woo
Attorney, Agent, or Firm—Kenyon & Kenyon

[57] ABSTRACT

A surgical instrument locking handle for securing the position of a first member with respect to a second member. The locking handle includes first and second members and has a locking slide attached to the first member. A locking wiper is attached at one end to the second member and has a free end that is in substantially continuous communication with the locking slide. Movement of the second member with respect to the first member is resisted by a frictional force created between the locking wiper and the locking slide. When a trigger is activated, however, that frictional force is reduced or eliminated, thereby allowing the previously locked members to move freely with respect to one another. The locking handle pursuant to the present invention provides a precise instrument that is easy to manufacture and efficient to use, and which eliminates the need for ridges or ribs on arm or handle members, or for latching mechanisms. When used in conjunction with a remotely manipulated surgical instrument, the locking handle of the present invention allows the surgeon to operate, lock, and unlock the instrument easily with one hand.

58 Claims, 7 Drawing Sheets

LOCKING HANDLE FOR SURGICAL INSTRUMENTS

FIELD OF THE INVENTION

The present invention relates generally to the field of surgical instruments, and more particularly to an improved locking handle for surgical instruments.

BACKGROUND OF THE INVENTION

In the prior art, various locking handles are disclosed for use with surgical instruments. The locking mechanism of these locking handles, however, are generally complex. Typically, the handle members of a locking handle actuate a remotely manipulated surgical instrument, such as jaw members, for use during a surgical procedure.

It is often necessary, however, for the surgeon or an assistant to maintain a constant force on the handle members to keep the remotely manipulated surgical instrument in a fixed position, such as closed. This is especially true when the remotely manipulated instrument is a grasping or gripping device such as a forcep, needle holder, clamp, or retractor. Having to maintain constant force on the handle members, however, limits the surgeon's effectiveness and/or may require yet additional personnel to be present in a crowded operating room (e.g., if an assistant is needed to hold the device in order to free up the surgeon).

To alleviate this problem, a locking mechanism may be used on the handle members, thereby allowing the surgeon using the instrument to lock the jaw member in place, such as in an open or a closed position. If a surgeon uses a locking handle (i.e., a handle with handle members and a locking mechanism), his hands can remain free to operate additional instruments during an operation. Furthermore, the use of a locking handle on a surgical instrument can free up the surgical assistant to assist the surgeon, rather than worry about holding the handle members in place, thereby eliminating the need for yet additional personnel in the operating room.

Typical locking handles include arm members that extend between the handle members so that a series of ridges or ribs on each arm member can engage a corresponding series of ridges or ribs on the opposite arm and thereby lock the handle members in place. Another type of locking handle has a latching mechanism, which usually is fixed at one end to one handle member and engages a series of ridges or ribs on the other handle member. This mechanism typically is released by bending one handle member in relation to the other, or by squeezing the handle members together, thereby disengaging the latching mechanism from the series of ridges or ribs. Examples of these types of locking handles are disclosed in U.S. Pat. No. 5,578,032 to Lalonde, U.S. Pat. No. 5,603,723 to Arani et al., U.S. Pat. No. 5,476,479 to Green et al., U.S. Pat. No. 5,342,391 to Foshee et al., and U.S. Pat. No. 4,896,661 to Bogert et al., each of which is incorporated herein by reference. A disadvantage associated with these handle members, however, is the manner in which their locking mechanisms are released.

Each time a surgeon wants to remove or reposition an instrument that includes a locking handle, he must disengage the locking mechanism. Locking mechanisms are commonly released by bending the handle members, which are typically constructed of a resilient material, such as stainless steel or rigid plastic. To release the locking mechanism, the surgeon must overcome the locking forces created by the natural flexing and biasing of the handle members. Typically this is accomplished by manually flexing the handle members away from each other. This procedure, however, usually requires the surgeon to use both of his hands, thereby causing the surgeon (or assistant) to cease whatever he is doing in order to release the mechanism. This, however, reduces the effectiveness of the surgeon (or assistant) during the operation.

Similarly, when a latching mechanism is used, the surgeon must squeeze the handle members together and disengage the latching mechanism. This procedure usually also requires the surgeon to use both of his hands—one to squeeze the handle members together and one to disengage the latching mechanism.

Accordingly, there remains a need for a locking handle for surgical instruments that avoids the disadvantages encountered with prior art locking handles and provides a precise instrument that is easy to manufacture and efficient to use. Such a locking handle preferably should not include any ridges or ribs on arm or handle members, or any latching mechanisms, thereby allowing a surgeon to use the surgical instrument with only one hand. Such a device would also preferably have an easy-to-use trigger for releasing the locking mechanism of the locking handle with only one hand.

SUMMARY OF THE INVENTION

In light of the above, a locking handle for surgical instruments is provided for securing the position of a second member with respect to a first member. The locking handle for surgical instruments includes first and second members and has a locking slide attached to the first member. A locking wiper is attached at one end to the second member and has a free end that is in substantially continuous communication with the locking slide. Movement of the second member with respect to the first member is resisted by a frictional force created between the locking wiper and the locking slide. When a trigger is activated, however, that frictional force is reduced or eliminated, thereby allowing the previously locked members to move freely with respect to one another.

BRIEF DESCRIPTION OF THE DRAWINGS

The invention will be more readily understood through the following detailed description, with reference to the accompanying drawings, in which.

DETAILED DESCRIPTION

The preferred embodiment of the present invention is a locking handle for a surgical instrument, such as a remotely manipulated forcep, needle holder, clamp, retractor, jaw members, spreaders, or similar device. The surgical instrument may be remotely manipulated in a number of ways, including using an actuation rod or a tension/release cable. Either arrangement may be used with the present invention, although the preferred embodiment of the invention will be discussed in conjunction with a surgical instrument that is remotely manipulated through an actuation rod.

Figure 1:
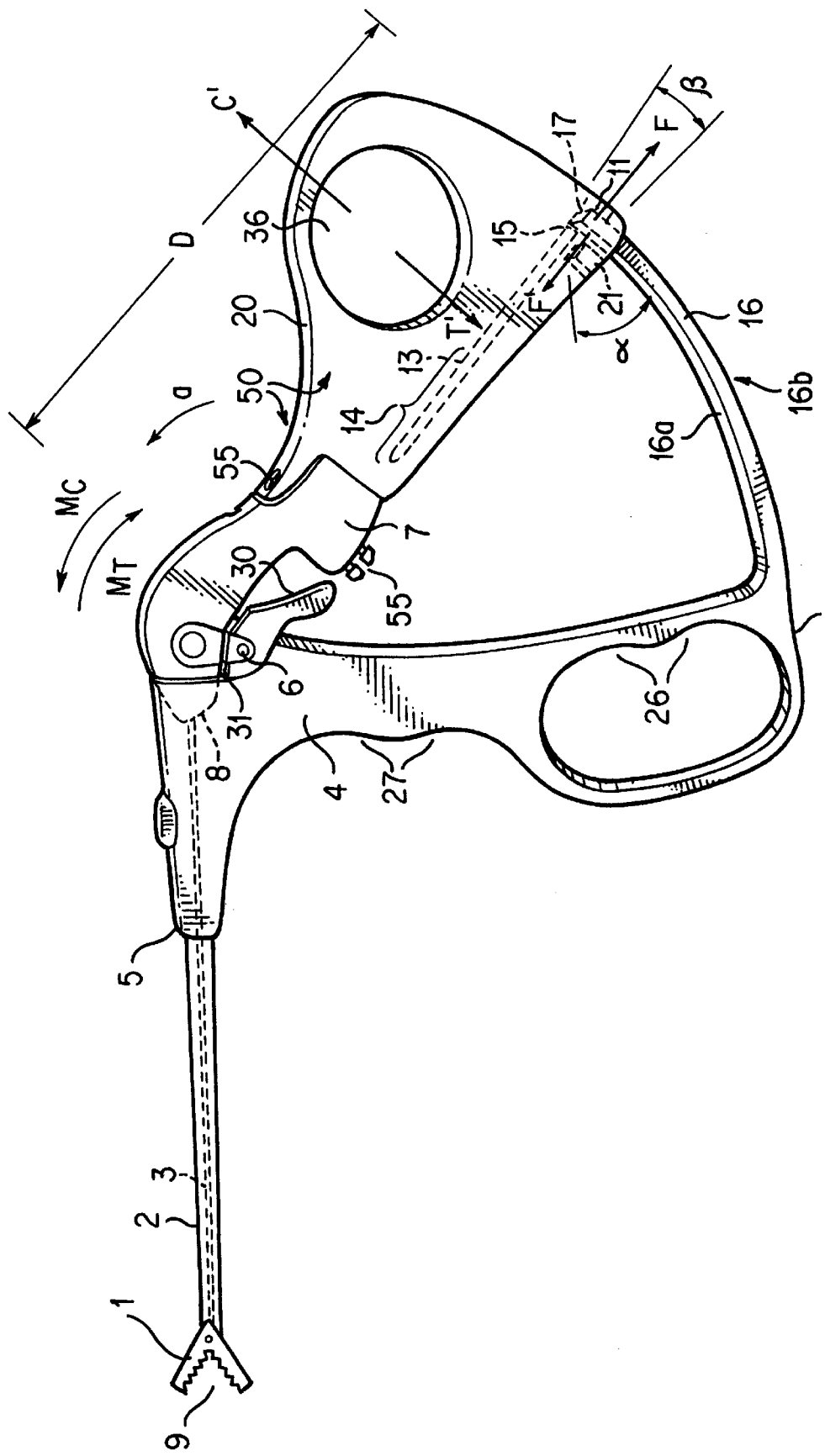
FIG. 1 is a perspective view, partially in section, of a locking handle for surgical instruments according to the preferred embodiment of the present invention.

As seen in FIG. 1, the present invention will be described in connection with a remotely manipulated instrument 1 that is separated from the locking handle by a rigid tube 2, preferably made out of a hardened metal such as steel. Inside the rigid tube 2 is an actuation rod 3 capable of carrying loads from the present invention to the remotely manipulated instrument 1.

The present invention includes a housing 4 to which the rigid tube 2 may be fixedly or removably attached at a tube connection point 5. The housing 4 may have a plurality of internally-molded finger grips 26 to facilitate the use of the present invention and it may have externally-molded finger grips 27 as well.

By the nature of its fixed connection to the remotely manipulated instrument 1 through the rigid tube 2, the housing 4 is designed to remain fixed with respect to the position of the remotely manipulated instrument 1 at all times.

A pivot 6 is attached to the housing 4, and is preferably made out of a metal, such as brass. An actuator 7 is loosely connected to the pivot 6, and the actuator 7 is rotatably movable about the pivot 6. In FIG. 1, however, the entire actuator 7 cannot be seen as the trigger shell 50 of the trigger 20 covers a substantial portion of the actuator 7. The interrelationship of the actuator 7, the trigger shell 50, and the trigger 20 will be more fully explained later with reference to FIGS. 2–4.

The actuation rod 3 is attached to the actuator 7 at a rod attachment point 8. Alternately, a tension/release cable may be attached to the actuator 7 in a similar manner.

When the actuator 7 is rotated about the pivot 6, the rotational movement of the actuator 7 creates a corresponding lateral movement of the actuation rod 3. This lateral movement of the actuation rod 3 causes the remotely manipulated instrument 1 to perform the desired function, such as closing its jaws 9 to grasp a remote object (not shown) when the actuator 7 is rotated about the pivot 6 in a clockwise direction (based on the orientation of the device in FIG. 1), or opening its jaws 9 to release the object when the actuator 7 is rotated about the pivot 6 in a counter-clockwise direction.

Alternately, a tension/release cable may be used to manipulate the instrument 1. When the actuator 7 is rotated about the pivot 6 in a clockwise direction, the rotational movement of the actuator 7 creates a tensile load in the cable and that load is transferred to the remotely manipulated instrument 1, which then performs the desired function, such as closing its jaws 9 to grasp a remote object. When the tensile load is released from the cable (i.e., the actuator 7 is rotated about the pivot 6 in a counter-clockwise direction), the remotely manipulated instrument 1 is free to revert back to its natural, pre-tensed position, such as by a spring (not shown) between jaws 9, or by some other restorative force.

When the actuator 7 in the preferred embodiment of the invention is rotated about the pivot 6 in a clockwise direction, the distal end 11 of the actuator 7 is brought in closer proximity to the distal end 12 of the housing 4. The range of rotational motion of the actuator 7 about the pivot 6 may be limited by the range of motion of the remotely manipulated instrument 1, or by the abutment of the actuator 7 against the housing 4 when the user of the present invention attempts to rotate the actuator 7 about the pivot 6 beyond its designed range of motion. In the preferred embodiment of the invention, the range of motion of the remotely manipulated instrument 1 (which is preferably a clamp) limits the rotation of the actuator 7 in the clockwise direction, and the range of motion in the counter-clockwise direction is limited by the abutment of the actuator 7 against the housing 4 at an actuator stop (not shown) near the rod attachment point 8. Alternately, the rotation of the actuator 7 in the clockwise direction about the pivot 6 may limited by the abutment of the actuator 7 against the housing 4 at an actuator stop 30, and the range of motion in the counter-clockwise direction may be limited by the abutment of the actuator 7 against the housing 4 at an actuator stop 31.

Figure 5:
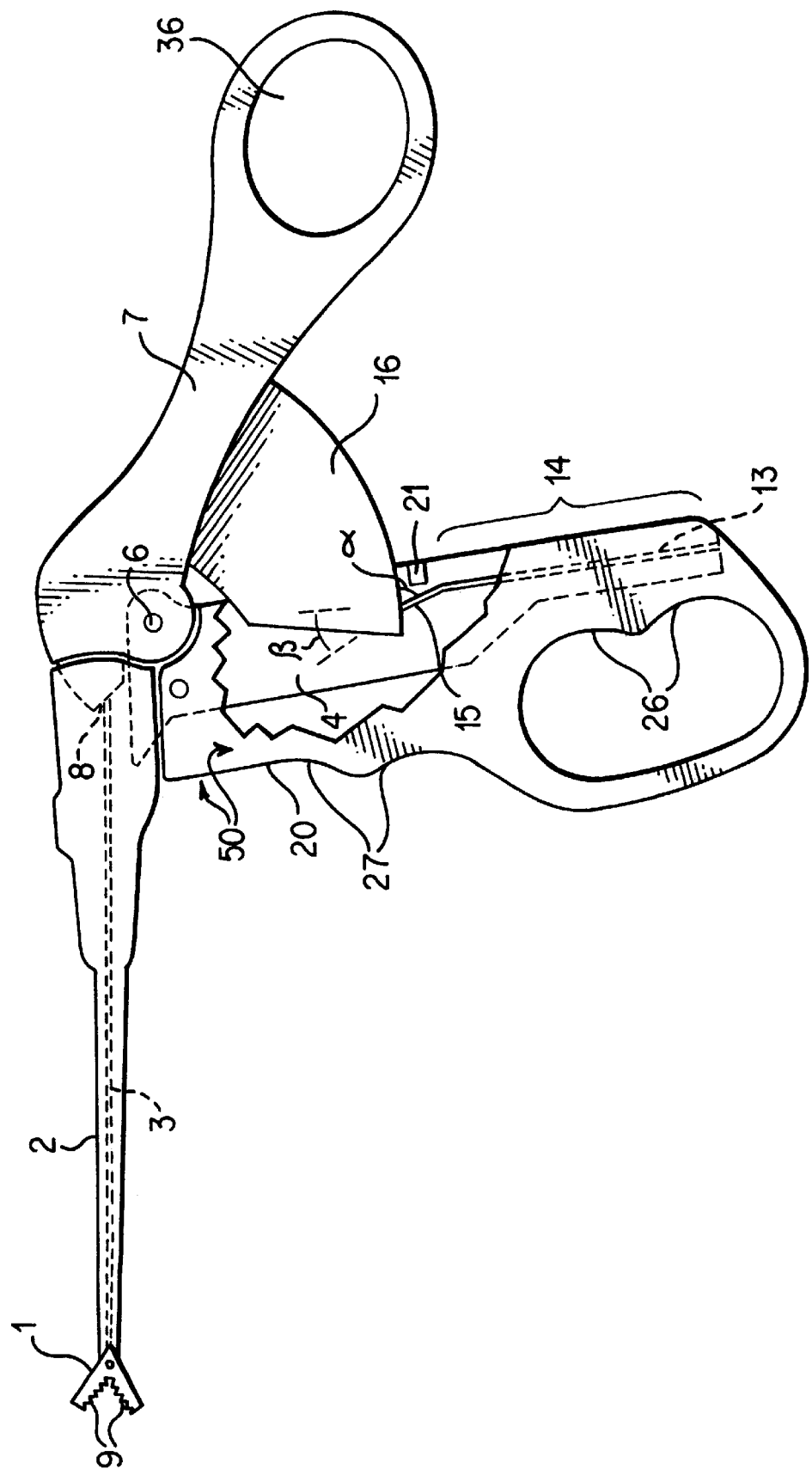
FIG. 5 is a partial plan view, partially in section, of a second embodiment of the invention.

In the preferred embodiment of the invention, a locking wiper 13 is fixedly attached to the actuator 7 along a fixed end 14 of the locking wiper 13. The locking wiper 13 has a free end 15 that is positioned to be in substantially continuous communication with a locking slide 16 extending from the housing 4. As seen in FIG. 5, however, the locking wiper 13 may alternately be attached to the housing 4 while the locking slide 16 extends from the actuator 7. Similarly, it is understood that, while the locking wiper 13 is generally referred to as a separate element attached to the actuator 7, the locking wiper 13 could be part of, or merely be an extension of, the actuator 7. Similarly, a portion of the housing 4 could function as the locking slide 16 without departing from the teaching of the present invention.

The free end 15 of the locking wiper 13 is designed to intersect the locking slide 16 at an angle $\alpha$ of less than ninety degrees. Because the free end 15 of the locking wiper 13 is bent away from the locking wiper 13 at an angle $\beta$, the natural tendency of the free end 15 is to revert to its undeformed state (i.e., to reduce $\beta$ to zero). Because the natural tendency of the free end 15 of the locking wiper 13 is to straighten itself out, a resulting force F is created from the free end 15 and into the portion 17 of the locking slide 16 in substantially continuous communication with the free end 15. Although portion 17 is shown in FIG. 1 to be only the end of the locking slide 16 in substantially continuous communication with the free end 15, it is understood that almost any portion of the locking slide 16 may be in substantially continuous communication with the free end 15 depending on the position the actuator 7 with respect to the housing 4.

The force F exerted on the portion 17 of the locking slide 16 from the free end 15 of the locking wiper 13 restricts the movement of the locking slide 16 with respect to the locking wiper 13. For the locking slide 16 to move with respect to the locking wiper 13, the locking slide 16 must overcome a self-energizing frictional force that exists between the locking slide 16 and the free end 15 of the locking wiper 13 as a result of force F. As the locking wiper 13 is attached to the actuator 7 and the locking slide 16 is attached to the housing 4, force F (and the corresponding self-energizing friction force created by force F) therefore restricts the movement of the actuator 7 with respect to the housing 4.

The frictional force is "self energizing" because as the moment $M_C$ created by the remotely grasped object increases (thereby increasing the tendency of the actuator 7 to rotate about the pivot 6 in the counter-clockwise direction), the moment $M_C$ drives the free end 15 of the locking wiper 13 more firmly into the locking slide 16. As a result, the resulting force F, and the corresponding frictional force created by force F, are increased, thereby allowing the present locking device to restrict the movement of the locking slide 16 with respect to the locking wiper 13 even under increasing loads.

Figure 4A:
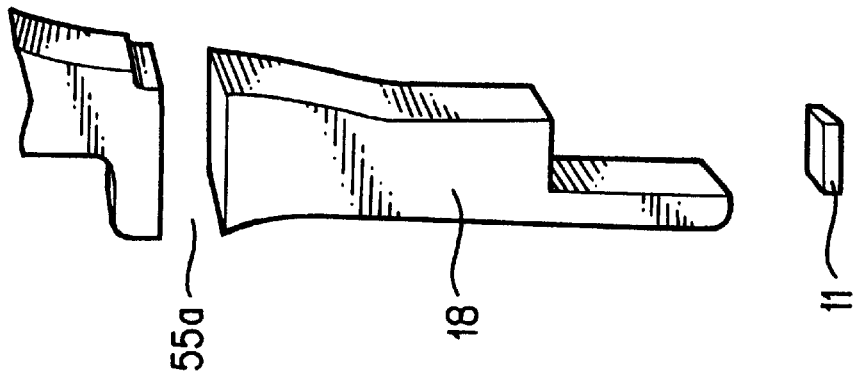
FIG. 4A is a perspective view of the actuator shown in FIG. 4, after the actuator shell has been removed.

The force F (and its corresponding frictional forces) restricting the movement of the actuator 7 with respect to the housing 4 may be augmented by having the locking slide 16 pass through the actuator 7, thereby dividing the actuator 7 into a main portion 18 and the distal end 11 (shown in FIG. 4A). Absent the distal end 11, the locking slide 16 may bend slightly (a "cantilever effect") in response to force F, thereby reducing the corresponding frictional force created by force F. The preferred embodiment of the invention, however, includes the distal end 11. Thus, in this configuration, when the force F acts on the portion 17 of the locking slide 16 in substantially continuous communication with the free end 15 of the locking wiper 13, that portion 17 is pressed into the distal end 11, and is thereby acted on by a force F' from the distal end 11 of the actuator 7. In this manner, the movement of the actuator 7 with respect to the housing 4 is more effectively resisted, as a second frictional force (due to F') is created that must also be overcome before the actuator 7 can move with respect to the housing 4.

The frictional forces created by forces F and F' may be augmented by increasing the surface friction of the locking slide 16 (or the distal end 11). One way that the surface friction of the locking slide 16 can be increased is by placing a rubber coating on the surface 16a of the locking slide 16 that engages the free end 15, and/or on the surface 16b of the locking slide 16 that engages the distal end 11 of the actuator 7. It is also known that one could likewise add a series of ridges (i.e., an "infinite rachet"), or any other type of frictional interface, on any surface of the locking slide 16 so as to increase its surface friction.

In its above-recited configuration, the present invention can effectively resist the movement of the actuator 7 with respect to the housing 4 in response to given moments $M_C$ and $M_T$ about the pivot 6. Moment $M_T$ can be defined as any moment created about the pivot 6 that tends to move the actuator 7 toward the housing 4 (i.e., in a clockwise direction, as shown in FIG. 1), thereby "tightening" the remotely manipulated instrument 1. Conversely, moment $M_C$ is any moment created about the pivot 6 that tends to move the actuator 7 away from the housing 4 (i.e., in a counter-clockwise direction, as shown in FIG. 1), thereby "releasing" the remotely manipulated instrument 1 slightly. The amount of moments $M_C$ and $M_T$ that a given configuration of the present invention can effectively resist varies proportionately to the distance D that the free end 15 of the locking wiper 13 is located away from the pivot 6.

In the preferred embodiment of the invention, the amount of moments $M_C$ and $M_T$ that the above-described configuration can effectively resist is comparable to the reasonable amount of moment created when the remotely manipulated instrument 1 properly performs its given function. For instance, if the remotely manipulated instrument 1 was designed to clamp onto a given item, the present invention would be designed to effectively resist any moment $M_C$ generated by the restorative forces created within the item when it is compressed. The amount of moments $M_C$ and $M_T$ that a given configuration can effectively resist should also account for those moments $M_C$ and $M_T$ reasonably created by external forces inadvertently acting on the present invention (e.g., a surgeon accidentally jostling the locking handle).

The meaning of the phrase "effectively resist" is that under a given moment load $M_C$ or $M_T$, the actuator 7 will not move with respect to the housing 4. In this manner, the present invention can be used as a "lock and forget" device, such that after the remotely manipulated instrument 1 is set to a certain position (represented by the position of the actuator 7 with respect to the housing 4), the remotely manipulated instrument 1 will not lose that set position, absent the influence of additional forces. Of course, should an additional force load be placed on the system (such as from the user of the present invention or from an increase in the restorative force created within the item being grasped by the remotely manipulated instrument 1), a given configuration may not be able to "effectively resist" the increased moment $M_C$ or $M_T$, and the actuator 7 may move with respect to the housing 4 and cause the remotely manipulated instrument 1 to loose its set position.

To facilitate the movement of the actuator 7 with respect to the housing 4 when it is desirable that the actuator 7 move in that manner, a trigger 20 is provided. It would be desirable to move the actuator 7 with respect to the housing 4 when the operator of the present invention wanted to increase or decrease the load carried from the present invention to the remotely manipulated instrument 1. The trigger 20 may be separately rotatable about the pivot 6 (see FIG. 6), it may be loosely attached to the housing 4 (see FIG. 5), or, as in the preferred embodiment of the invention, it may be loosely attached to the actuator 7 (see FIG. 1).

The design of the trigger 20 is such that when the trigger 20 is activated, a foot 21 engages the free end 15 of the locking wiper 13 and disrupts the substantially continuous communication between the free end 15 and the portion 17 of the locking slide 16 directly beneath the free end 15. In this manner, the force F created between the free end 15 and the portion 17 of the locking slide 16 is substantially reduced or eliminated, thereby reducing or eliminating the associated friction force between the free end 15 and the portion 17 of the locking slide 16, and allowing the actuator 7 to move more easily with respect to the housing 4. Similarly, the reduction or elimination of the force F reduces or eliminates force F' and its associated frictional force (assuming the design includes a distal end 11, as in the preferred embodiment of the invention).

In the preferred embodiment of the invention, the trigger 20 is activated by applying a force C' at a thumb grip 36, which is incorporated into the trigger 20. As the trigger 20 slidably engages the actuator 7 (such that a substantial portion of the actuator 7 is contained within the trigger shell 50), and the trigger 20 is connected to the actuator 7 only through a fastener 55, the application of the force C' at the thumb grip 36 causes much of the trigger 20 to attempt to rotate about the fastener 55 in the direction a. As a result, the foot 21 of the trigger 20 move in the direction of the force C' and applies pressure on the free end 15 of the locking wiper 13 in the direction of the force C'. The application of pressure in the direction of the force C' may also be referred to as applying pressure in the direction of the locking wiper 13 (i.e., relative to the position of the foot 21).

In the preferred embodiment of the invention, it is desirable to apply pressure in the direction of the locking wiper 13 because the application of this pressure increases the angle β of deflection between the free end 15 of the locking wiper 13 and the locking wiper 13 itself. This, in turn, disrupts the substantially continuous communication between the free end 15 and the portion 17 of the locking slide 16 directly beneath the free end 15, and thereby reduces or eliminates the force F exerted on the locking slide 16 by the free end 15 of the locking wiper 13. The application of a force T' at the thumb grip 36, however, causes the foot 21 of the trigger 20 to move away from the locking wiper 13 and therefore not apply any force. Instead, the trigger 20 contacts the actuator 7 along an interface line 41 (shown in FIG. 2A) and moves the actuator 7 in the direction of the housing 4. In the preferred embodiment of the invention, the movement of the actuator 7 in the direction of the housing 4 "tightens" the remotely manipulated clamp 1.

Figure 2A:
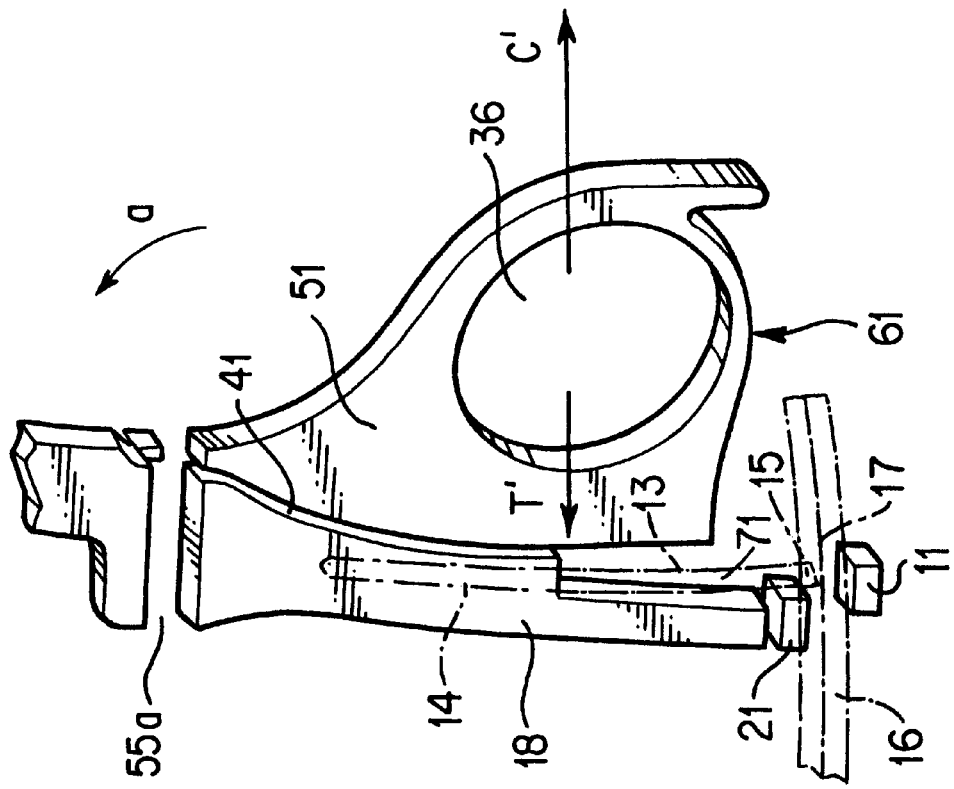
FIG. 2A is a perspective view, partially in section, of the actuator and trigger shown in FIG. 2, after the actuator shell and the trigger shell have been removed.
Figure 2:
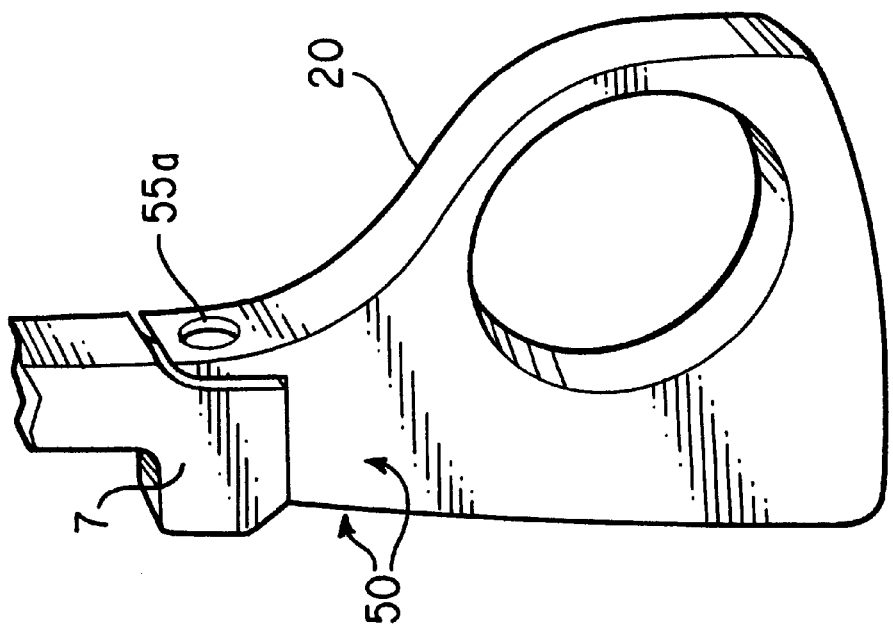
FIG. 2 is a perspective view of the actuator and trigger used in the preferred embodiment of the present invention.
Figure 3A:
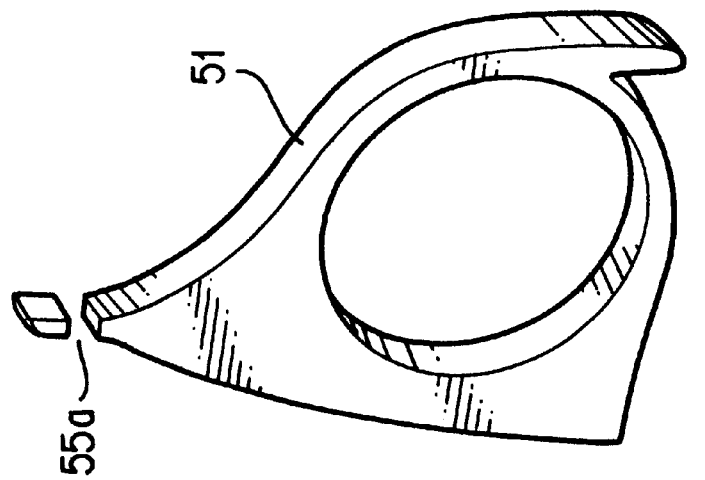
FIG. 3A is a perspective view of the trigger shown in FIG. 3, after the trigger shell has been removed.
Figure 3:
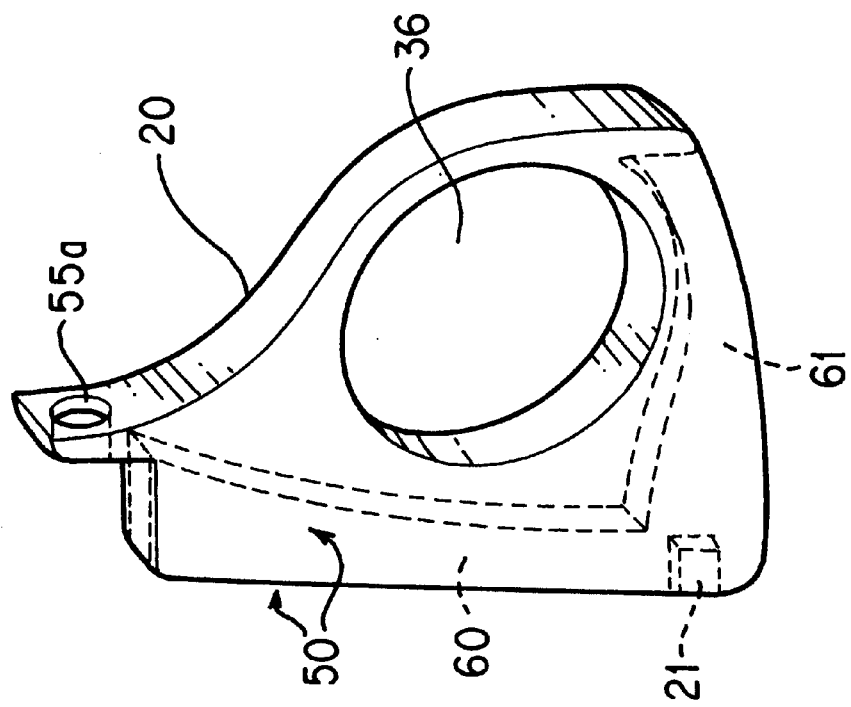
FIG. 3 is a perspective view, partially in section, of the trigger used in the preferred embodiment of the present invention.
Figure 4:
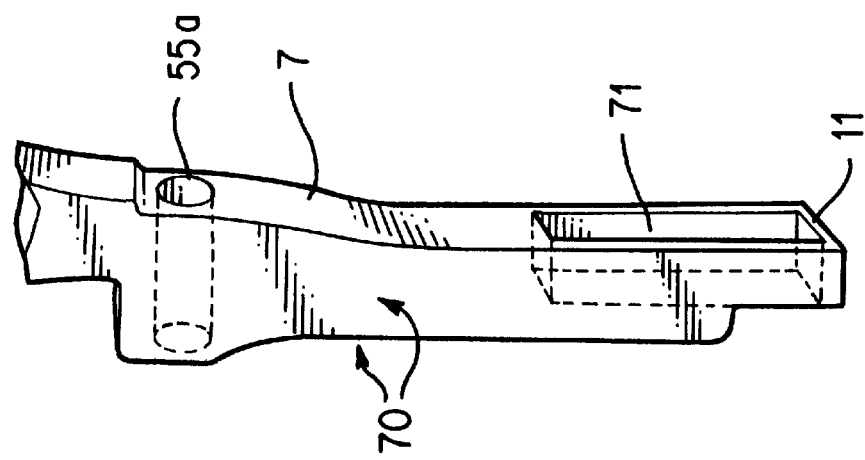
FIG. 4 is a perspective view, partially in section, of the actuator used in the preferred embodiment of the present invention.

The interrelationship between the trigger 20 and the actuator 7 can be seen in FIGS. 2–4. Reference will first be made to FIGS. 3 and 4 (showing the trigger 20 and the actuator 7 respectively), however, as these two parts together form the component shown in FIG. 2 (the fastener 55 is not shown in FIGS. 2–4, thereby leaving a fastener hole 55a).

In FIG. 3, the trigger 20 is shown. The trigger shell 50 covers both sides of the trigger 20. When the trigger shell 50 is removed, however, one can see the internal structure of the trigger 20 (shown in FIG. 3A). As seen in FIG. 3A, the trigger 20 has a connecting piece 51, which provides the structure for the trigger 20 and connects the sides of the trigger shell 50 together. As can be seen by comparing FIGS. 3 and 3A, the trigger shell 50 and the connecting piece 51 together define openings 60 and 61, which will receive the actuator 7 and the locking slide 16 respectively when the trigger 20 is incorporated into the completed device. The foot 21 of the trigger 20 is not connected to the connecting piece 51, but is connecting to both sides of the trigger shell 50.

With reference to FIG. 4, the actuator 7 is shown. Much like the trigger 20, the actuator has a shell 70 that covers the main portion 18 of the actuator 7. Accordingly, the actuator 7 defines a opening 71, which is for receiving a substantial portion of the locking wiper 13 (i.e., that portion of the locking wiper 13 that is not fixedly connected to the actuator 7). As can be seen by comparing FIGS. 4 and 4A, the distal end 11 of the actuator is not connected to the main portion 18, but is connected to both sides of the actuator shell 70.

Finally, as can be seen in FIG. 2, the actuator 7 and the trigger 20 slidably engage one another for use in the present invention. In FIG. 2A, the internal structure of the both the actuator 7 and the trigger 20 can be seen as both the actuator shell 70 and the trigger shell 50 have been removed. The locking wiper 13 and a portion of the locking slide 16 are also shown in FIG. 2A (albeit with dotted lines), so that the relationship among the free end 15 of the locking wiper 13, the foot 21, the locking slide 16 and 17, and the distal end 11 of the actuator 7 may be shown.

Still with reference to FIG. 2A, when a force C' is applied to the thumb grip 36, the trigger shell 50, the connecting piece 51, and the foot 21 will move in the direction of the force C', and thereby attempt to rotate about the fastener 55 in the direction a. These components will move slightly about the fastener 55 because of the flexing inherent in the material that comprises the components. Accordingly, the movement about the fastener 55, is very slight.

Nonetheless, the movement of these components about the fastener 55 will cause the foot 21 to apply pressure on the free end 15 of the locking wiper 13 in the direction of the locking wiper 13, thereby reducing the forces F and F' (shown in FIG. 1) created by the interaction of the free end 15 and the locking slide 16. As explained previously, the reduction or elimination of theses forces F and F' reduces or eliminates the associated frictional forces and will allow the actuator 7 to move freely with respect to the housing 4, and this movement will create a moment $M_C$ about the pivot 6, thereby opening the remotely manipulated instrument 1 in the preferred embodiment of the invention.

If, however, a force T' is applied at the thumb grip 36, the trigger shell 50, the connecting piece 51, and the foot 21 will move in the direction of the force T', and the foot 21 will move away from the locking wiper 13 and therefore not apply any pressure on the free end 15. Instead, the connecting piece 51 of the trigger 20 will contact the main portion 18 of the actuator 7 along the interface line 41. As a result, the force T' will also act on the actuator 7 and move the actuator 7 and the trigger 20 in the direction of the housing 4. This movement will tighten the remotely manipulated instrument 1 in the preferred embodiment of the invention by creating a moment $M_T$ about the pivot 6.

It is also appreciated the trigger 20 may be capable of "automatic" triggering, such that when the surgeon grips the handle members of the present invention, he will automatically engage the trigger 20. This, in turn, will cause the foot 21 to engage the free end 15 of the locking wiper 13 and reduce or eliminate forces F and F', thereby allowing the actuator 7 to move freely with respect to the housing 4. When the surgeon release his grip on the handle members, however, the foot 21 of the trigger 20 will disengage from the locking wiper 13, and forces F and F' would once again create corresponding frictional forces that would secure the position of the actuator 7 with respect to the housing 4.

An alternative embodiment of the present invention is shown in FIG. 5, in which the locking wiper 13 is attached to the housing 4, and the locking slide 16 is attached to the actuator 7. Accordingly, finger grips 26 comprise part of the trigger 20 rather than the housing 4. In addition, a portion of the trigger shell 50 shown in FIG. 5 has been "cut away" to better illustrate the internal structure of the invention.

Figure 6:
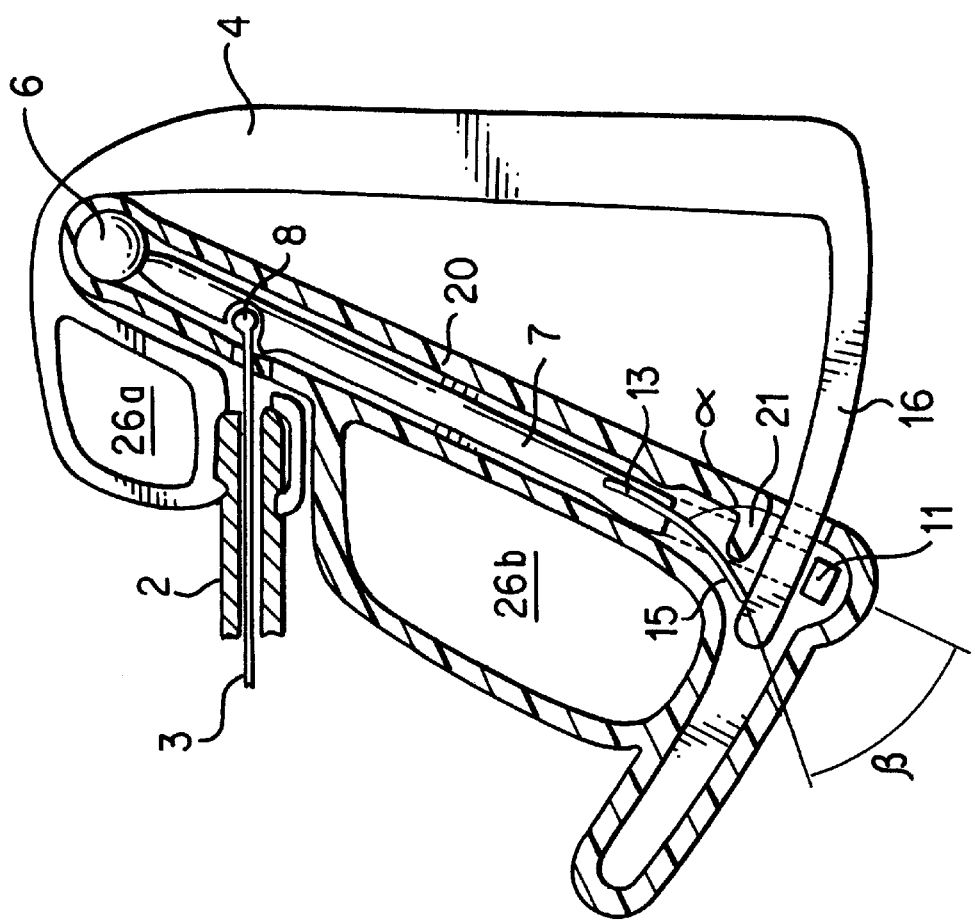
FIG. 6 is a partial plan view, partially in section, of a third embodiment of the invention.

Still another embodiment of the present invention is shown in FIG. 6, in which the actuator 7 is located forward of the housing 4. In this particular embodiment, one of the finger grips 26a is part of the housing 4, while the other 26b is part of the trigger 20.

Figure 7:
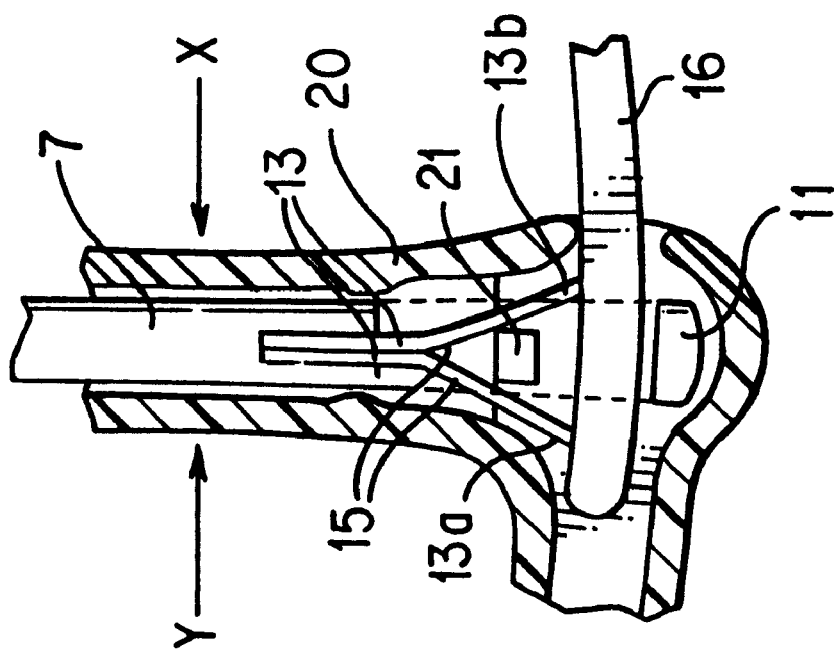
FIG. 7 is a sectional view of a dual locking design that may be used with any embodiment of the present invention.

All of the embodiments of the present invention are also capable of using a dual locking device (shown in FIG. 7) in which two locking wipers 13 are used. One reason for using two locking wipers 13 is because a single locking device (as used in FIGS. 1, 5, and 6) is primarily designed to effectively resist moments (such as $M_C$ in FIG. 1) that have the effect of increasing the resultant force F by decreasing the angle β of deflection of the free end 15 of the locking wiper 13 (i.e., driving the free end 15 more firmly into the locking slide 16). With a dual locking device, however, the locking handle would be able to resist loads in both directions with approximately equal effectiveness.

When using a dual locking device, the trigger 20 may be designed with a foot 21 that has a cross-beam (not shown) that extends between the free ends 15 of the locking wipers 13. With this configuration, the trigger 20 may be used to selectively deactivate either locking wiper 13. For example, when pressure is applied on the trigger 20 in the direction x, the foot 21 will apply pressure on, and deactivate, locking wiper 13a. Similarly, when pressure is applied on the trigger 20 in the direction y, the foot 21 will apply pressure on, and deactivate, locking wiper 13b.

Still other objects and advantages of the present invention will become readily apparent to those skilled in this art from the above-recited detailed description, wherein only the preferred embodiment of the invention has been shown and described. The description of the preferred embodiment is simply by way of illustration of the best mode contemplated for carrying out the invention. As will be realized, the invention is capable of other and different embodiments, and its several details are capable of modification in various respects, all without departing from the invention. Accordingly, the drawings and descriptions are to be regarded as illustrative in nature, and not as restrictive.

What is claimed is:

1. A surgical instrument locking device for securing the position of a second member with respect to a first member comprising:
   a. a first member having a locking end;
   b. a second member having a substantially flexible free end, said substantially flexible free end being in substantially continuous communication with said locking end; and
   c. wherein movement of said second member with respect to said first member is resisted by a frictional force created between said substantially flexible free end and said locking end in response to said movement of said second member.

2. The device as recited in claim 1, wherein said first member is rotatably movable relative to said second member.

3. The device as recited in claim 2, further comprising:
   a cable attached to said second member; and
   wherein said movement of said second member applies a force to said cable in a generally horizontal direction and actuates an instrument located remote to said second member.

4. The device as recited in claim 2, further comprising:
   a cable attached to said first member; and
   wherein movement of said first member applies a force to said cable in a generally horizontal direction and actuates an instrument located remote to said first member.

5. The device as recited in claim 1, further comprising:
   a trigger for moving said substantially flexible free end with respect to said locking end.

6. The device as recited in claim 5, wherein when said trigger is activated, said frictional force created between said substantially flexible free end and said locking end in response to said movement of said second member is substantially reduced.

7. The device as recited in claim 6, wherein said second member is rotatably movable about a pivot attached to said first member.

8. The device as recited in claim 7, wherein said first member is a handle.

9. The device as recited in claim 8, wherein said locking end passes through said second member.

10. The device as recited in claim 9, wherein said second member is a handle.

11. The device as recited in claim 6, wherein said trigger is rotatably movable about a pivot.

12. The device as recited in claim 11, wherein said pivot is attached to said first member.

13. The device as recited in claim 12, wherein said trigger is activated by applying a force to said trigger.

14. The device as recited in claim 13, wherein said trigger further comprises:
   a foot for engaging said substantially flexible free end when said force is applied to said trigger.

15. The device as recited in claim 6, wherein said trigger is activated by applying a force to said trigger.

16. The device as recited in claim 15, wherein said trigger further comprises:
   a foot for engaging said substantially flexible free end when said force is applied to said trigger.

17. The device as recited in claim 6, wherein said trigger is attached to said first member.

18. A surgical instrument locking device for securing the position of a second member with respect to a first member comprising:
   a. a first member having a locking end;
   b. a second member having a free end, said free end being in substantially continuous communication with said locking end;
   c. wherein movement of said second member with respect to said first member is resisted by a frictional force created between said free end and said locking end in response to said movement of said second member; and
   d. an actuation rod attached to said second member.

19. The device as recited in claim 18, wherein said movement of said second member moves said actuation rod in a generally horizontal direction.

20. The device as recited in claim 19, wherein said movement of said actuation rod in a generally horizontal direction actuates an instrument.

21. The device as recited in claim 20, wherein said instrument is located remote to said second member.

22. A surgical instrument locking device for securing the position of a second member with respect to a first member comprising:
   a. a first member having a locking end;
   b. a second member having a free end, said free end being in substantially continuous communication with said locking end;
   c. wherein movement of said second member with respect to said first member is resisted by a frictional force created between said free end and said locking end in response to said movement of said second member; and
   d. an actuation rod attached to said first member.

23. The device as recited in claim 22, wherein movement of said first member moves said actuation rod in a generally horizontal direction.

24. The device as recited in claim 23, wherein said movement of said actuation rod in a generally horizontal direction actuates an instrument.

25. The device as recited in claim 24, wherein said instrument is located remote to said first member.

26. A surgical instrument locking device for securing the position of a second member with respect to a first member comprising:
   a. a first member having a locking end;
   b. a second member having a free end, said free end being in substantially continuous communication with said locking end;
   c. wherein movement of said second member with respect to said first member is resisted by a frictional force created between said free end and said locking end in response to said movement of said second member;
   d. a trigger for moving said free end with respect to said locking end;
   e. wherein when said trigger is activated, said frictional force created between said free end and said locking end in response to said movement of said second member is substantially reduced; and f. wherein said second member is an actuator and said first member is a housing.

27. A surgical instrument locking device for securing the position of an actuator with respect to a housing comprising:
   a. a housing;
   b. a pivot attached to said housing;
   c. an actuator rotatably moveable about said pivot;
   d. a locking slide attached to said actuator;
   e. a locking wiper having a fixed end and a free end, said fixed end being attached to said housing and said free end being in substantially continuous communication with said locking slide, wherein movement of said actuator with respect to said housing is resisted by a frictional force created between said free end of said locking wiper and said locking slide in response to said movement of said actuator; and
   f. a trigger connected to said housing, wherein when said trigger is activated, said trigger substantially reduces said frictional force created between said free end of said locking wiper and said locking slide in response to said movement of said actuator.

28. A surgical instrument locking device for securing the position of an actuator with respect to a housing comprising:
   a. a housing;
   b. a pivot attached to said housing;
   c. an actuator rotatably moveable about said pivot;
   d. a locking slide attached to said housing;
   e. a locking wiper having a fixed end and a free end, said fixed end being attached to said actuator and said free end being in substantially continuous communication with said locking slide, wherein movement of said actuator with respect to said housing is resisted by a frictional force created between said free end of said locking wiper and said locking slide in response to said movement of said actuator; and
   f. a trigger connected to said actuator, wherein when said trigger is activated, said trigger substantially reduces said frictional force created between said free end of said locking wiper and said locking slide in response to said movement of said actuator.

29. A locking device for a surgical instrument, said surgical instrument having an elongated tube, an actuation rod disposed within said tube, said actuation rod having a distal end, and a remotely-manipulated instrument coupled to said distal end of said actuation rod, said locking device comprising:
   a. a housing connected to said elongated tube;
   b. a pivot attached to said housing;
   c. an actuator rotatably moveable about said pivot, said actuator being moveably coupled to said housing and connected to said actuation rod;
   d. an arcuate locking slide attached to said actuator;
   e. a locking member;
   f. a trigger coupled to said housing;
   g. wherein a portion of said locking slide is in substantially continuous communication with said locking member;
   h. wherein movement of said actuator with respect to said housing is resisted by a frictional force created between said locking member and said portion of said locking slide in response to said movement of said actuator;
   i. wherein when said trigger is activated, said frictional force created between said locking member and said portion of said locking slide in response to said movement of said actuator is reduced, thereby allowing said actuator to move with respect to said housing;
   j. wherein rotation of said actuator about said pivot creates a lateral movement of said actuation rod through said elongated tube that actuates said remotely-manipulated instrument; and
   k. wherein said portion of said locking slide in substantially continuous communication with said locking member has a smooth and uniform surface.

30. The device as recited in claim 29, wherein said locking member has a free end and said portion of said locking slide is in substantially continuous communication with said locking member proximate said free end of said locking member.

31. The device as recited in claim 30, wherein said actuator includes an internally-molded thumb grip.

32. The device as recited in claim 31, wherein said remotely-manipulated instrument comprises moveable jaw members that close when said rotation of said actuator is in a clockwise direction and that open when said rotation of said actuator is in a counter-clockwise direction.

33. The device as recited in claim 29, wherein said locking member is contained within said housing, wherein said housing defines a cavity, and wherein said portion of said locking slide is in substantially continuous communication with said locking member within said cavity.

34. The device as recited in claim 33, wherein said portion of said locking slide is in substantially continuous communication with said locking member proximate said free end of said locking member.

35. The device as recited in claim 34, wherein said remotely-manipulated instrument comprises moveable jaw members that close when said rotation of said actuator is in a clockwise direction and that open when said rotation of said actuator is in a counter-clockwise direction.

36. The device as recited in claim 35, wherein said actuator includes an internally-molded thumb grip.

37. A locking device for a surgical instrument, said locking device comprising:
   a. a housing, said housing defining a cavity;
   b. a pivot attached to said housing;
   c. an actuator rotatably moveable about said pivot and moveably connected to said housing;
   d. an arcuate locking slide attached to said actuator;
   e. a locking member, said locking member having a free end within said cavity;
   f. a trigger coupled to said housing;
   g. wherein a portion of said locking slide is in substantially continuous communication with said locking member within said cavity;
   h. wherein movement of said actuator with respect to said housing is resisted by a frictional force created between said locking member and said portion of said locking slide in response to said movement of said actuator;
   i. wherein when said trigger is activated, said frictional force created between said locking member and said portion of said locking slide in response to said movement of said actuator is reduced, thereby allowing said actuator to move with respect to said housing; and
   i. wherein said portion of said locking slide in substantially continuous communication with said locking member has a smooth and uniform surface.

38. The device as recited in claim 37, wherein said portion of said locking slide is in substantially continuous communication with said locking member proximate said free end of said locking member.

39. The device as recited in claim 38, wherein said surgical instrument has an elongated tube, a cable disposed within said tube, said cable having a distal end, and a remotely-manipulated instrument coupled to said distal end of said cable, and wherein:

said housing is connected to said elongated tube;

said actuator is connected to said cable; and rotation of said actuator about said pivot in a clockwise direction creates tension in said cable that actuates said remotely-manipulated instrument.

40. The device as recited in claim 37, wherein said surgical instrument has an elongated tube, an actuation rod disposed within said tube, said actuation rod having a distal end, and a remotely-manipulated instrument coupled to said distal end of said actuation rod, and wherein:

said housing is connected to said elongated tube;

said actuator is connected to said actuation rod; and rotation of said actuator about said pivot creates a lateral movement of said actuation rod through said elongated tube that actuates said remotely-manipulated instrument.

41. The device as recited in claim 40, wherein said remotely-manipulated instrument comprises moveable jaw members that close when said rotation of said actuator is in a clockwise direction and that open when said rotation of said actuator is in a counter-clockwise direction.

42. The device as recited in claim 41, wherein said actuator includes an internally-molded thumb grip.

43. The device as recited in claim 41, wherein said portion of said locking slide is in substantially continuous communication with said locking member proximate said free end of said locking member.

44. The device as recited in claim 41, wherein said locking member has a fixed end attached to said housing and wherein a portion of said locking slide has a rubber coating.

45. A locking device for a surgical instrument, said surgical instrument having an elongated tube, an actuation rod disposed within said tube, said actuation rod having a distal end, and a remotely-manipulated instrument coupled to said distal end of said actuation rod, said locking device comprising:

a. a housing connected to said elongated tube;

b. a pivot attached to said housing;

c. an actuator rotatably moveable about said pivot, said actuator being moveably coupled to said housing and connected to said actuation rod;

d. an arcuate locking slide attached to said housing;

e. a locking member;

f. a trigger coupled to said actuator;

g. wherein a portion of said locking slide is in substantially continuous communication with said locking member;

h. wherein movement of said actuator with respect to said housing is resisted by a frictional force created between said locking member and said portion of said locking slide in response to said movement of said actuator;

i. wherein when said trigger is activated, said frictional force created between said locking member and said portion of said locking slide in response to said movement of said actuator is reduced, thereby allowing said actuator to move with respect to said housing;

j. wherein rotation of said actuator about said pivot creates a lateral movement of said actuation rod through said elongated tube that actuates said remotely-manipulated instrument; and k. wherein said portion of said locking slide in substantially continuous communication with said locking member has a smooth and uniform surface.

46. The device as recited in claim 45, wherein said locking member has a free end and said portion of said locking slide is in substantially continuous communication with said locking member proximate said free end of said locking member, and wherein said actuator includes an internally-molded thumb grip and said housing includes an internally-molded finger grip.

47. The device as recited in claim 46, wherein said remotely-manipulated instrument comprises moveable jaw members that close when said rotation of said actuator is in a clockwise direction and that open when said rotation of said actuator is in a counter-clockwise direction.

48. The device as recited in claim 45, wherein said locking member is contained within said actuator, wherein said actuator defines a cavity, and wherein said portion of said locking slide is in substantially continuous communication with said locking member within said cavity.

49. The device as recited in claim 48, wherein said portion of said locking slide is in substantially continuous communication with said locking member proximate said free end of said locking member.

50. The device as recited in claim 49, wherein said remotely-manipulated instrument comprises moveable jaw members that close when said rotation of said actuator is in a clockwise direction and that open when said rotation of said actuator is in a counter-clockwise direction and wherein said actuator includes an internally-molded thumb grip and said housing includes an internally-molded finger grip.

51. A locking device for a surgical instrument, said locking device comprising:

a. a housing;

b. a pivot attached to said housing;

c. an actuator rotatably moveable about said pivot and moveably connected to said housing, said actuator defining a cavity;

d. an arcuate locking slide attached to said housing;

e. a locking member, said locking member having a free end within said cavity;

f. a trigger coupled to said actuator;

g. wherein a portion of said locking slide is in substantially continuous communication with said locking member within said cavity;

h. wherein movement of said actuator with respect to said housing is resisted by a frictional force created between said locking member and said portion of said locking slide in response to said movement of said actuator;

i. wherein when said trigger is activated, said frictional force created between said locking member and said portion of said locking slide in response to said movement of said actuator is reduced, thereby allowing said actuator to move with respect to said housing; and j. wherein said portion of said locking slide in substantially continuous communication with said locking member has a smooth and uniform surface.

52. The device as recited in claim 51, wherein said portion of said locking slide is in substantially continuous communication with said locking member proximate said free end of said locking member.

53. The device as recited in claim 52, wherein said surgical instrument has an elongated tube, a cable disposed within said tube, said cable having a distal end, and a remotely-manipulated instrument coupled to said distal end of said cable, and wherein:

said housing is connected to said elongated tube;
said actuator is connected to said cable; and
rotation of said actuator about said pivot in a clockwise direction creates tension in said cable that actuates said remotely-manipulated instrument.

54. The device as recited in claim 51, wherein said surgical instrument has an elongated tube, an actuation rod disposed within said tube, said actuation rod having a distal end, and a remotely-manipulated instrument coupled to said distal end of said actuation rod, and wherein:

said housing is connected to said elongated tube;
said actuator is connected to said actuation rod; and
rotation of said actuator about said pivot creates a lateral movement of said actuation rod through said elongated tube that actuates said remotely-manipulated instrument.

55. The device as recited in claim 54, wherein said remotely-manipulated instrument comprises moveable jaw members that close when said rotation of said actuator is in a clockwise direction and that open when said rotation of said actuator is in a counter-clockwise direction.

56. The device as recited in claim 55, wherein said actuator includes an internally-molded thumb grip and said housing includes an internally-molded finger grip.

57. The device as recited in claim 55, wherein said portion of said locking slide is in substantially continuous communication with said locking member proximate said free end of said locking member.

58. The device as recited in claim 55, wherein said locking member has a fixed end attached to said housing and wherein a portion of said locking slide has a rubber coating.

\* \* \* \* \*